(12) United States Patent
Nishikawa et al.

(10) Patent No.: US 10,058,258 B2
(45) Date of Patent: Aug. 28, 2018

(54) BIOMAGNETISM MEASURING DEVICE, BIOMAGNETISM MEASURING SYSTEM, AND BIOMAGNETISM MEASURING METHOD

(75) Inventors: Takuo Nishikawa, Fussa (JP); Yasuo Ando, Sendai (JP)

(73) Assignees: KONICA MINOLTA ADVANCED LAYERS, INC., Tokyo (JP); Tohoku University, Miyagi (JP)

( * ) Notice: Subject to any disclaimer, the term of this patent is extended or adjusted under 35 U.S.C. 154(b) by 40 days.

(21) Appl. No.: 13/822,291

(22) PCT Filed: Aug. 30, 2011

(86) PCT No.: PCT/JP2011/069509
§ 371 (c)(1),
(2), (4) Date: Mar. 11, 2013

(87) PCT Pub. No.: WO2012/032962
PCT Pub. Date: Mar. 15, 2012

(65) Prior Publication Data
US 2013/0165766 A1    Jun. 27, 2013

(30) Foreign Application Priority Data
Sep. 10, 2010  (JP) ................... 2010-202540

(51) Int. Cl.
*A61B 5/04* (2006.01)
*A61B 5/00* (2006.01)
(Continued)

(52) U.S. Cl.
CPC ...... *A61B 5/04007* (2013.01); *A61B 5/04008* (2013.01); *A61B 5/6803* (2013.01);
(Continued)

(58) Field of Classification Search
CPC ... A61B 5/04; A61B 5/04005; A61B 5/04007; A61B 5/04008; A61B 5/6803;
(Continued)

(56) References Cited

U.S. PATENT DOCUMENTS 5,442,289 A * 8/1995 Dilorio ............. A61B 5/04008
                                                324/248
6,424,853 B1 * 7/2002 Tsukada et al. ............. 600/409
(Continued)

FOREIGN PATENT DOCUMENTS

CN    1651928    8/2005
EP    1227526    7/2002
(Continued)

OTHER PUBLICATIONS

Guerrero et al., "Low frequency noise in arrays of magnetic tunnel junctions connected in series and parallel", Jun. 9 2009, Journal of Applied Physics, 105, 113922-1 through 113922-5.*

(Continued)

*Primary Examiner* — Katherine Fernandez
(74) *Attorney, Agent, or Firm* — Cozen O'Connor

(57) ABSTRACT

A biomagnetism measuring device includes a magnetic sensor and a support unit. The magnetic sensor includes a tunnel magneto-resistive element including a fixed magnetic layer, a free magnetic layer and an insulating layer. The insulating layer is disposed between the fixed magnetic layer and the free magnetic layer, and has resistance being changed by a tunnel effect depending on an angle difference between a direction of magnetization of the fixed magnetic layer and a direction of magnetization of the free magnetic layer. The support unit supports the magnetic sensor in such a way that the tunnel magneto-resistive element faces a living body. The magnetic sensor outputs an output signal in accordance with a resistance value of the insulating layer, (Continued)

the resistance value being changed by magnetism emitted from the living body.

2 Claims, 11 Drawing Sheets

(51) Int. Cl.
| | |
|---|---|
| *B82Y 25/00* | (2011.01) |
| *G01R 33/09* | (2006.01) |
| *G01R 33/12* | (2006.01) |
| *H01F 10/32* | (2006.01) |
| *H01L 27/22* | (2006.01) |
| *H01L 29/82* | (2006.01) |

(52) U.S. Cl.
CPC ............ *B82Y 25/00* (2013.01); *G01R 33/093* (2013.01); *G01R 33/1269* (2013.01); *H01F 10/3254* (2013.01); *H01L 27/22* (2013.01); *A61B 2562/0223* (2013.01); *A61B 2562/046* (2013.01); *H01L 29/82* (2013.01)

(58) Field of Classification Search
CPC ...... A61B 2562/0223; A61B 2562/046; B82Y 25/00; G01R 33/093; G01R 33/1269; H01F 10/3254; H01L 27/22; H01L 29/82
USPC .......................................................... 600/409
See application file for complete search history.

(56) References Cited

U.S. PATENT DOCUMENTS

| | | | | |
|---|---|---|---|---|
| 2002/0142490 | A1* | 10/2002 | Sato et al. ........................ | 438/3 |
| 2004/0232912 | A1* | 11/2004 | Tsukamoto et al. .......... | 324/248 |
| 2005/0200854 | A1* | 9/2005 | Wilson ............... | A61B 5/04008 |
| | | | | 356/456 |
| 2005/0230827 | A1* | 10/2005 | Naito ..................... | G01R 33/02 |
| | | | | 257/737 |
| 2005/0270020 | A1* | 12/2005 | Peczalski ............. | B82Y 25/00 |
| | | | | 324/247 |
| 2008/0008908 | A1 | 1/2008 | Ishiwata et al. | |
| 2009/0072823 | A1* | 3/2009 | Wan .................... | G01R 33/0206 |
| | | | | 324/247 |
| 2010/0138183 | A1* | 6/2010 | Jensen ............... | A61B 19/5244 |
| | | | | 702/150 |

FOREIGN PATENT DOCUMENTS

| | | |
|---|---|---|
| JP | 02-040578 | 2/1990 |
| JP | 03-001839 | 1/1991 |
| JP | 10-070325 | 3/1998 |
| JP | 2000-193364 | 7/2000 |
| JP | 2004-065605 | 3/2004 |
| JP | 2004-093576 | 3/2004 |
| JP | 2004-93576 | 3/2004 |
| JP | 2007-017248 | 1/2007 |
| JP | 2009-297224 | 12/2009 |
| WO | WO 2006/054469 | 5/2006 |
| WO | WO 2008/102299 | 8/2008 |

OTHER PUBLICATIONS

"Fibre-reinforced plastic", in Wikipedia, Online Access Date: Jun. 11, 2015, URL: http://en.wikipedia.org/wiki/Fibre-reinforced_plastic.*
Search Report dated Jan. 28, 2014 issued in the corresponding European Patent Application No. 11 82 3438.
K. Tsukada, "Non-invasive measurement of the currents in the human body", Journal of the Japan Society of Applied Electromagnetics and Mechanics, vol. 13, No. 2, pp. 119-124, Jun. 2005.
S. Yokota et al., "Tunnel magnetoresistance and noise in magnetic tunnel junction array", Extended abstracts; The Japan Society of Applied Physics, Aug. 30, 2010, 14p-J-6.
M. Tondra, et al., "Picotesla field sensor design using spin-dependent tunneling devices", J. Applied Physics, vol. 18, No. 11, Jun. 1, 1998.
R.C. Chaves, et al., "Low frequency picotesla field detection using hybrid MgO based tunnel sensors", Applied Physics Letters 91, 102504 American Institute of Physics 91, 102504, 2007.
Search Report dated Sep. 5, 2017 which issued in the corresponding European Patent Application No. 11823438.4.

* cited by examiner

BIOMAGNETISM MEASURING DEVICE, BIOMAGNETISM MEASURING SYSTEM, AND BIOMAGNETISM MEASURING METHOD

RELATED APPLICATIONS

This is a U.S. national stage of application No. PCT/JP2011/069509, filed on Aug. 30, 2011.

This patent application claims the priority of Japanese application no. 2010-202540 filed Sep. 10, 2010, the disclosure content of which is hereby incorporated by reference.

FIELD OF THE INVENTION

The present invention relates to a biomagnetism measuring device, a biomagnetism measuring system, and a biomagnetism measuring method.

BACKGROUND OF THE ART

Conventionally, as a device to measure magnetism emitted from a living body, a biomagnetism measuring device using SQUID (Superconducting Quantum Interference Device) sensors has been researched (Patent Documents 1 to 5 or the like). By arranging a large number of SQUID sensors, and using the SQUID sensors to measure the biomagnetism, two-dimensional magnetism information, such as magnetoencephalograms and magnetocardiograms, can be obtained.

To measure the biomagnetism with the SQUID sensors, the SQUID sensors need to be maintained in a superconductive state with a refrigerant. Hence, the SQUID sensors are placed in a Dewar flask where a refrigerant is stored, and used for the measurement in a state in which the SQUID sensors are soaked in the refrigerant.

There has been proposed a biomagnetism measuring device in which a portion of an outer wall part of a refrigerant tank of a Dewar flask is formed in a shape fit for a measurement target part of a living body, such as a skull, many SQUID sensors are arranged in the outer wall part so as to be soaked in a refrigerant, and the outside of the outer wall part touches the living body, and consequently the SQUID sensors are close to the living body with a certain distance, and the measurement is performed so that a magnetoencephalogram or the like can be obtained.

RELATED ART DOCUMENT

Patent Document

Patent Document 1: Japanese Patent Application Laid-Open Publication No. hei 2-40578
Patent Document 2: Japanese Patent Application Laid-Open Publication No. hei 3-1839
Patent Document 3: Japanese Patent Application Laid-Open Publication No. 2000-193364
Patent Document 4: Japanese Patent Application Laid-Open Publication No. 2004-65605
Patent Document 5: Japanese Patent Application Laid-Open Publication No. 2007-17248

Non-Patent Document

Non-Patent Document 1: JOURNAL OF APPLIED PHYSICS, VOLUME 83 NUMBER 11, 1 Jun. 1998, "Picotesla field sensor design using spin-dependent tunneling devices" copyright: 1998 American Institute of Physics.
Non-Patent Document 2: APPLIED PHYSICS LETTERS 91, 102504(2007), "Low frequency picotesla field detection using hybrid MgO based tunnel sensors" copyright: 2007 American Institute of Physics.

SUMMARY OF THE INVENTION

The Problems to be Solved by the Invention

However, a biomagnetism measuring device using SQUID sensors have the following problems.

A refrigerant to maintain the SQUID sensors at a low temperature is reduced by evaporation or the like. Hence, management of the refrigerant is complicated, and a refrigerant tank which is thermally insulated needs to be configured.

A sensor unit in which the SQUID sensors to be close to a living body at the time of the measurement are disposed, namely, a Dewar flask storing the refrigerant therein, is large and heavy. Hence, a mechanical configuration to support the sensor unit is needed. In addition, usually, a bed to place a subject and a position control device which controls relative positions of the subject and the Dewar flask in which the SQUID sensors are disposed are needed.

Body sizes and body shapes of subjects vary depending on their ages, sexes or the like. It is difficult to configure a Dewar flask which can make the arrangement of the SQUID sensors fit for a target part of a subject flexibly. Hence, there is a case where the SQUID sensors cannot be disposed in such a way as to keep a certain distance to the target part regardless of subjects. Accordingly, the measurement cannot be accurately performed, or the measurement itself cannot be performed.

The SQUID sensors are large, so that it is difficult to dispose many SQUID sensors close to the surface of a living body, such as the scalp, at high density. Hence, only the magnetism emitted from the surface of a living body in a direction perpendicular to the surface thereof is measured, and it is difficult to measure the magnetism in an in-plane direction of the surface of the living body.

By being able to measure magnetic forces of the magnetism, which is emitted from a living body, not only in a direction of one axis, such as a direction perpendicular to the surface of the living body, the direction in which the magnetism is measured by the SQUID sensors, but in directions of three axes, which are, for example, the direction of one axis perpendicular to the surface of a living body and directions of two axes at right angles to each other being in-plane directions of the surface of the living body, it becomes possible to obtain more magnetism information, and use the magnetism information for diagnosis.

However, magnetic sensors, which do not need cooling mechanisms, used for a magnetism recording reading device or the like do not have the sensitivity the same as or close to that of the SQUID sensors. In fact, such magnetic sensors are not sensors to measure weak biomagnetism, such as brain-magnetism, from the beginning.

The present invention is made in view of the problems of the conventional technologies, and objects thereof include providing a biomagnetism measuring device, a biomagnetism measuring system and a biomagnetism measuring method each of which measures the biomagnetism at high accuracy with magnetic sensors which can be used at a normal temperature.

Means for Solving the Problems

In order to solve at least one of the problems described above, the present invention includes a biomagnetism measuring device including: a magnetic sensor including: a tunnel magneto-resistive element including: a fixed magnetic layer in which a direction of magnetization is fixed; a free magnetic layer in which a direction of magnetization is changed by being influenced by a magnetic flux from outside; and an insulating layer disposed between the fixed magnetic layer and the free magnetic layer, and having resistance being changed by a tunnel effect depending on an angle difference between the direction of the magnetization of the fixed magnetic layer and the direction of the magnetization of the free magnetic layer; and a support unit which supports the magnetic sensor in such a way that the tunnel magneto-resistive element faces a living body, wherein the magnetic sensor outputs an output signal in accordance with a resistance value of the insulating layer, the resistance value being changed by magnetism emitted from the living body.

The present invention disclosed includes the biomagnetism measuring device wherein the magnetic sensor includes a tunnel magneto-resistive element array in which a plurality of the tunnel magneto-resistive elements is arranged in a lattice, and outputs the output signal from a shared output terminal provided for the tunnel magneto-resistive elements.

The present invention disclosed includes the biomagnetism measuring device wherein bonding faces of the fixed magnetic layers and the insulating layers and/or bonding faces of the free magnetic layers and the insulating layers of the tunnel magneto-resistive elements are disposed on a shared plane.

The present invention disclosed includes the biomagnetism measuring device wherein the shared plane is along a direction perpendicular to a measurement target part of the living body.

The present invention disclosed includes the biomagnetism measuring device wherein the magnetic sensor includes a first tunnel magneto-resistive element array in which the direction of the magnetization of the fixed magnetic layer is fixed in a first direction, and a second tunnel magneto-resistive element array in which the direction of the magnetization of the fixed magnetic layer is fixed in a second direction which intersects with the first direction.

The present invention disclosed includes the biomagnetism measuring device wherein the magnetic sensor includes a third tunnel magneto-resistive element array in which the direction of the magnetization of the fixed magnetic layer is fixed in a third direction which is at right angles to the first direction and the second direction.

The present invention disclosed includes the biomagnetism measuring device including a sensor assembly including a plurality of the magnetic sensors.

The present invention disclosed includes the biomagnetism measuring device including a plurality of the sensor assemblies.

The present invention disclosed includes a biomagnetism measuring system including: the biomagnetism measuring device and an arithmetic device which calculates a magnetoencephalogram on the basis of the output signal.

The present invention disclosed includes a biomagnetism measuring method including: supporting a magnetic sensor in such a way that a tunnel magneto-resistive element faces a living body, the magnetic sensor including the tunnel magneto-resistive element including: a fixed magnetic layer in which a direction of magnetization is fixed; a free magnetic layer in which a direction of magnetization is changed by being influenced by a magnetic flux from outside; and an insulating layer disposed between the fixed magnetic layer and the free magnetic layer, and having resistance being changed by a tunnel effect depending on an angle difference between the direction of the magnetization of the fixed magnetic layer and the direction of the magnetization of the free magnetic layer; and measuring magnetism of a living body on the basis of an output signal in accordance with a resistance value of the insulating layer from the magnetic sensor, the resistance value being changed by the magnetism emitted from the living body.

The present invention disclosed includes the biomagnetism measuring method wherein the magnetic sensor includes a tunnel magneto-resistive element array in which a plurality of the tunnel magneto-resistive elements is arranged in a lattice, and the magnetism of the living body is measured on the basis of the output signal from the tunnel magneto-resistive element array.

The present invention disclosed includes the biomagnetism measuring method wherein the magnetic sensor outputs the output signal with respect to the magnetism emitted in a direction perpendicular to a measurement target part of the living body.

The present invention disclosed includes the biomagnetism measuring method wherein the magnetic sensor outputs the output signal with respect to the magnetism, which is emitted from the living body, in directions of two axes being at right angles to each other.

The present invention disclosed includes the biomagnetism measuring method wherein the magnetic sensor outputs the output signal with respect to the magnetism, which is emitted from the living body, in directions of three axes being at right angles to each other.

The present invention disclosed includes the biomagnetism measuring method wherein a plurality of the magnetic sensors is included.

Advantageous Effects of the Invention

According to the present invention, the tunnel magneto-resistive (TMR) element applied to the biomagnetism measurement can constitute a highly sensitive element, and hence can measure biomagnetic fields accurately. In addition, because the magnetic sensor can be used at a normal temperature, the sensor unit to be close to a living body at the time of the measurement does not need a refrigerant for cooling the TMR element, and hence the sensor unit can be configured lighter and thinner.

Because the sensor unit can be configured lighter and thinner, the sensor unit can be configured in a simple and flexible form so as to be able to be handled by hand, and to be placed on and cover a measurement target part of a subject, or be worn by a subject. Further, because the sensor unit has high sensitivity, and does not need a cooling mechanism, the size thereof is not large, and magnetic sensors having a few restrictions to be disposed on a living body can be configured.

Therefore, it is easy to dispose the magnetic sensors close to a living body, and the biomagnetic fields can be measured more accurately. Further, even if a plurality of magnetic sensors is used, they can be disposed close to each other. Hence, the biomagnetic fields can be measured far more accurately.

EMBODIMENT FOR CARRYING OUT THE INVENTION

In the following, an embodiment of the present invention is described with reference to the drawings. The following is an embodiment of the present invention, and hence does not intend to limit the present invention.

The embodiment is with respect to biomagnetism measurement to obtain a magnetoencephalogram by measuring magnetism emitted from a skull of a person.

Figure 1:
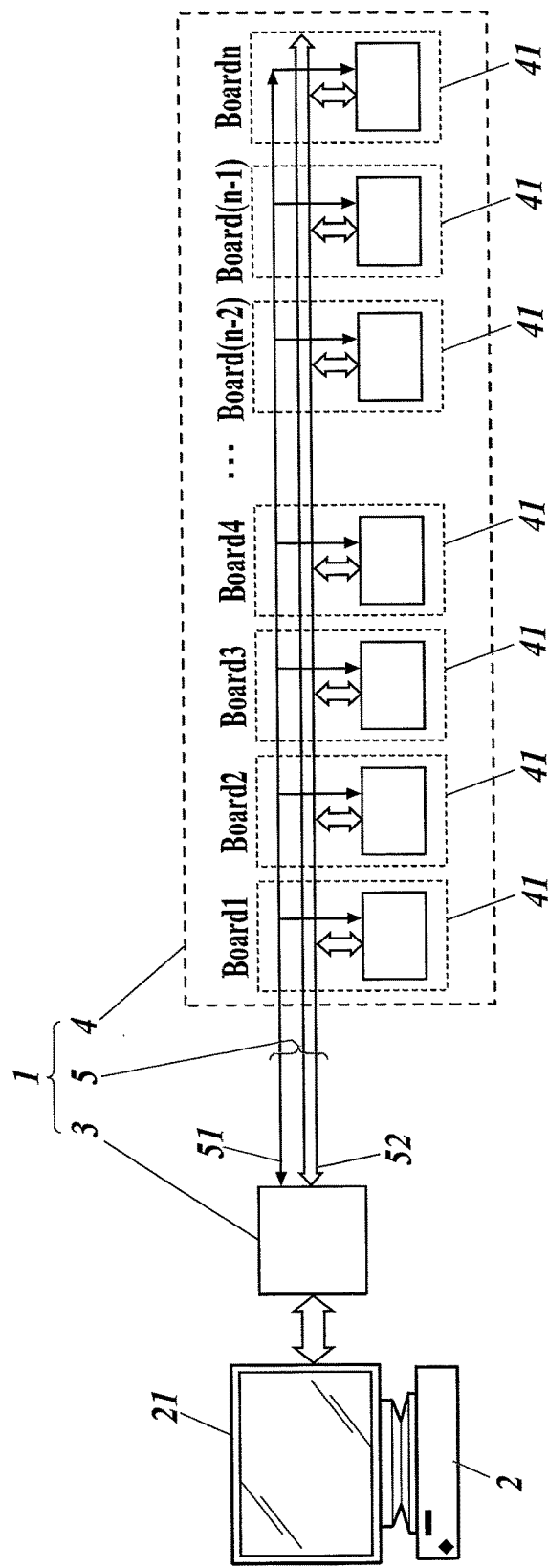
FIG. 1 is a block diagram showing the whole configuration of a biomagnetism measuring device and a biomagnetism measuring system in accordance with an embodiment of the present invention.

As shown in FIG. 1, a biomagnetism measuring system 100 of the embodiment includes a biomagnetism measuring device 1 and an arithmetic device 2. The biomagnetism measuring device 1 includes an interface 3 and a sensor unit 4.

The arithmetic device 2 and the sensor unit 4 are connected to each other via the interface 3. The sensor unit 4 and the interface 3 are connected to each other with a cable 5 so that the sensor unit 4 can be freely moved and turned around within an area where the cable 5 reaches. The "51" represents a power line, and the "52" represents a signal line (bus).

The sensor unit 4 includes a plurality of sensor platform boards 41, and power is supplied thereto by the power line 51. Command signals are transmitted to the sensor platform boards 41 from the arithmetic device 2, and output signals are transmitted to the arithmetic device 2 from the sensor platform boards 41, via the signal line 52. The number of sensor platform boards 41 is represented by "n" (n being an integer of two or more).

A display device 21 is connected to the arithmetic device 2. The display device 2 is used for displaying arithmetic results or the like.

Figure 2:
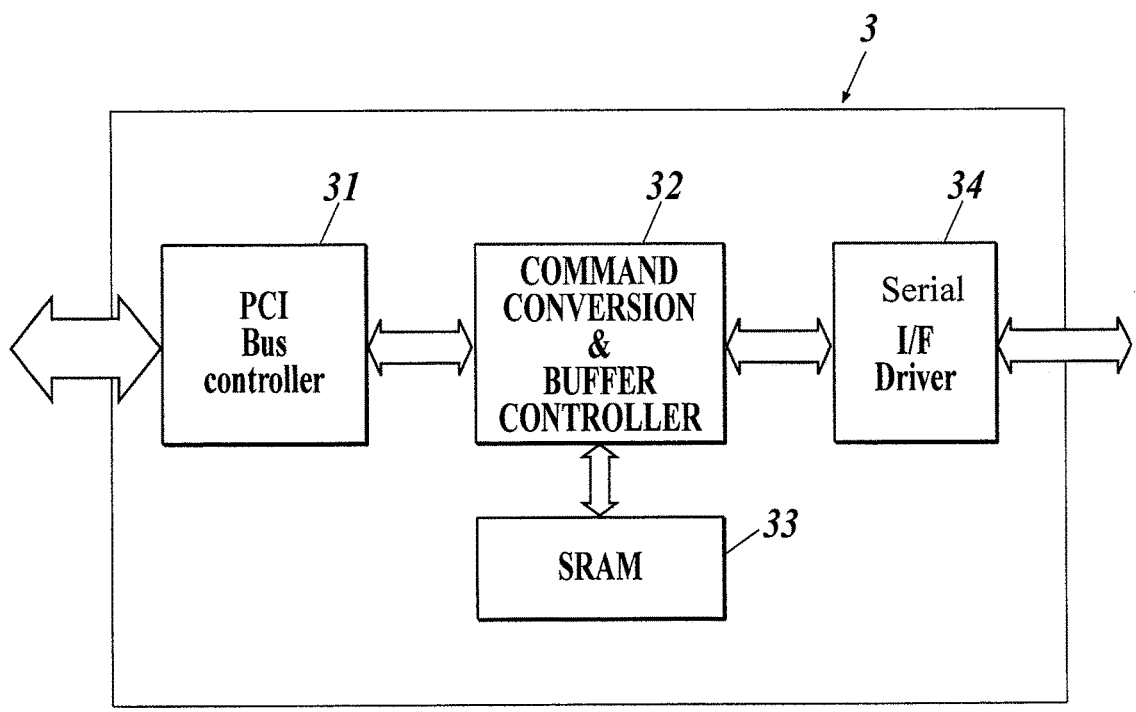
FIG. 2 is a block diagram of an interface in accordance with the embodiment of the present invention.

As shown in FIG. 2, the interface 3 includes a PCI bus controller 31, a command conversion & buffer controller 32, an SRAM 33 and a serial interface driver 34. The driver 34, the controller 31 and the controller 32 control a controller and a bus, which are described below, disposed in each board 41, and temporarily store signals as needed in the SRAM 33, so that the output signals are sent from the boards 41 serially.

As shown in FIG. 3, a plurality of TMR array modules 6 is electrically connected and mechanically fixed to a sensor platform board 41. The sensor platform board 41 constitutes a sensor assembly including a plurality of magnetic sensors.

Figure 3A:
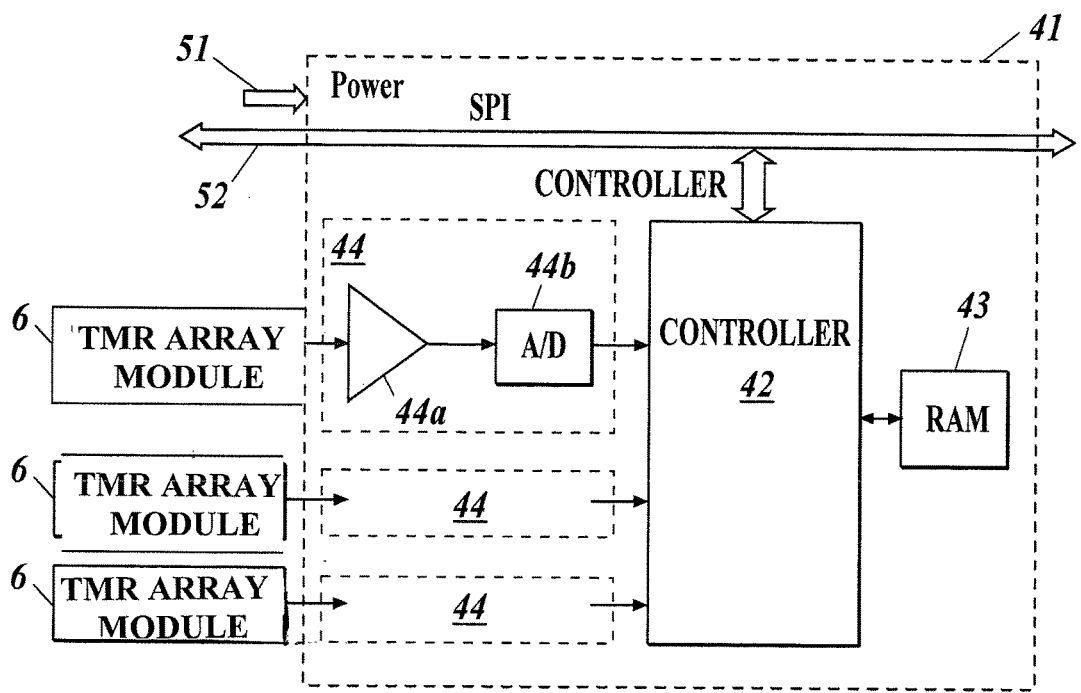
FIG. 3A is a block diagram showing a configuration of a sensor platform board in accordance with the embodiment of the present invention.

As shown in FIG. 3A, the sensor platform board 41 includes a controller 42, a RAM 43 and a plurality of amplifier & converter circuits 44. The amplifier & converter circuits 44 are provided for the TMR array modules 6, respectively, and connected to the TMR array modules 6 one to one. An amplifier & converter circuit 44 includes an amplifier 44a, which amplifies output signals from the TMR array module 6, and an A/D converter 44b, which converts output of the amplifier 44a into digital signals to input the signals into the controller 42. The RAM 43 is a storage device, which stores information inputted into the controller 42 and information calculated by the controller 42. The controller 42 receives commands from the arithmetic device 2, and operates the TMR array modules 6 so as to send out the output signals thereof in a predetermined format to the arithmetic device 2 via the signal line 52.

Figure 3B:
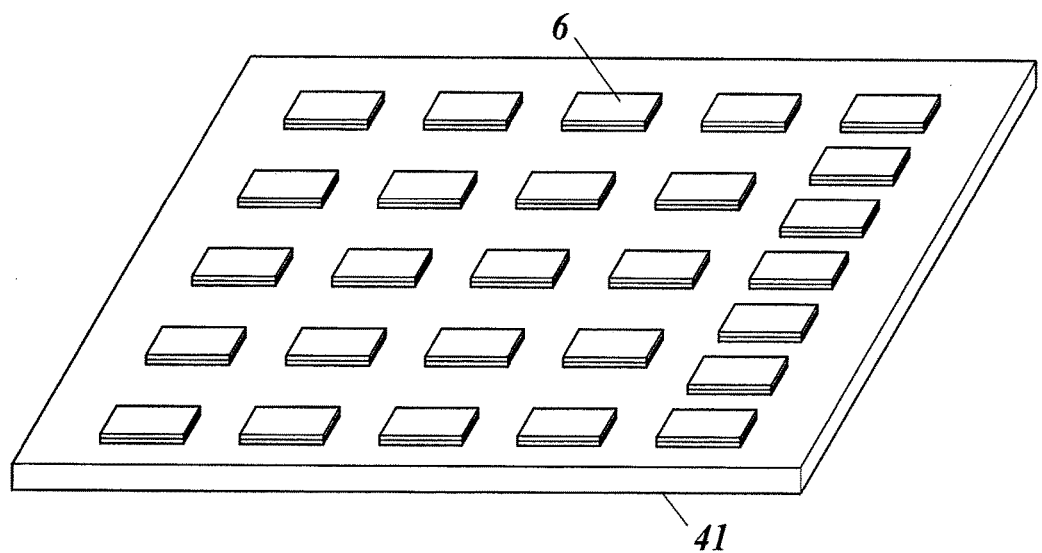
FIG. 3B is a perspective view of an external appearance of the sensor platform board in accordance with the embodiment of the present invention.
Figure 4A:
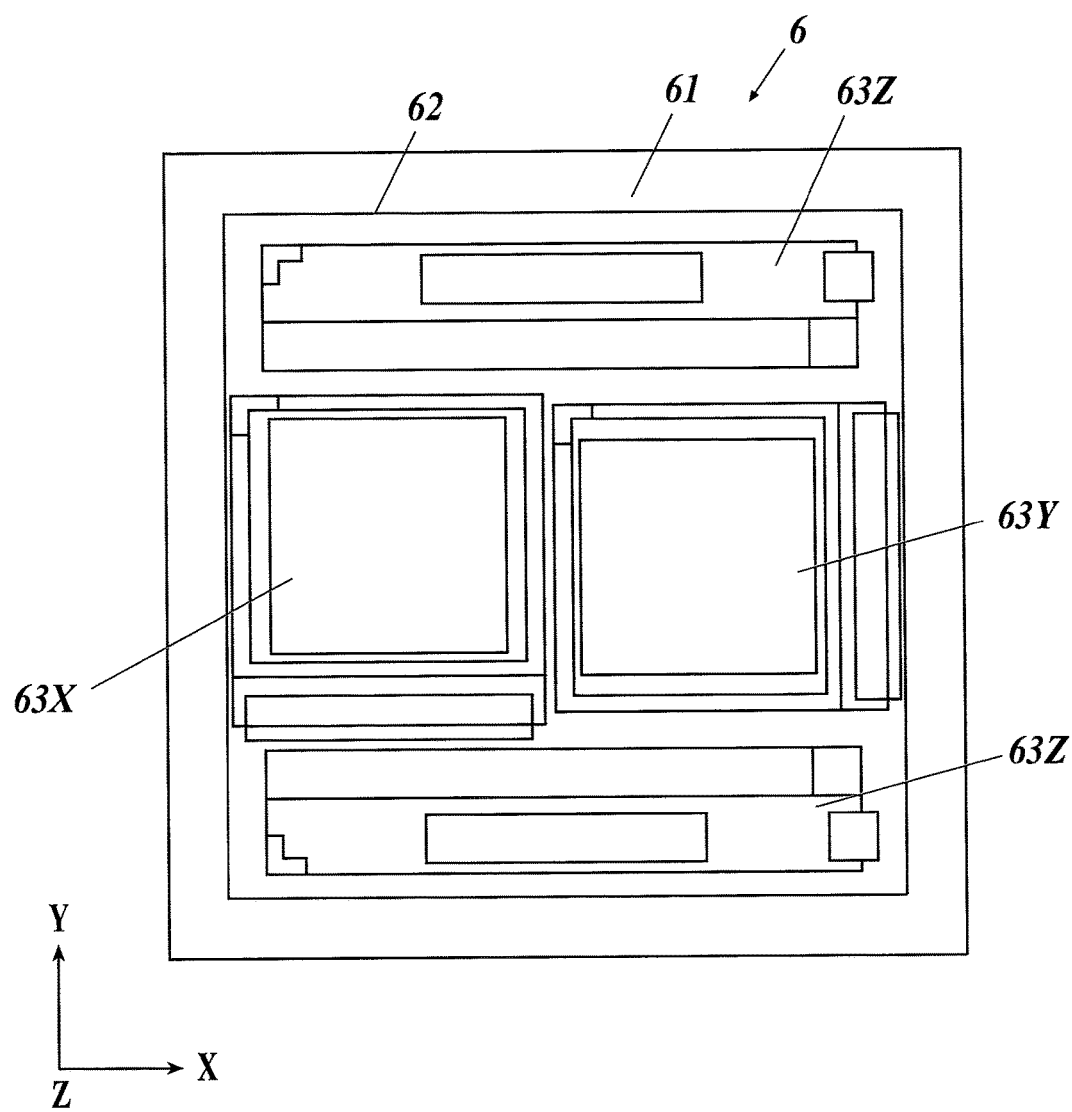
FIG. 4A is a perspective/plan view showing the inside of a TMR array module in accordance with the embodiment of the present invention.
Figure 4B:
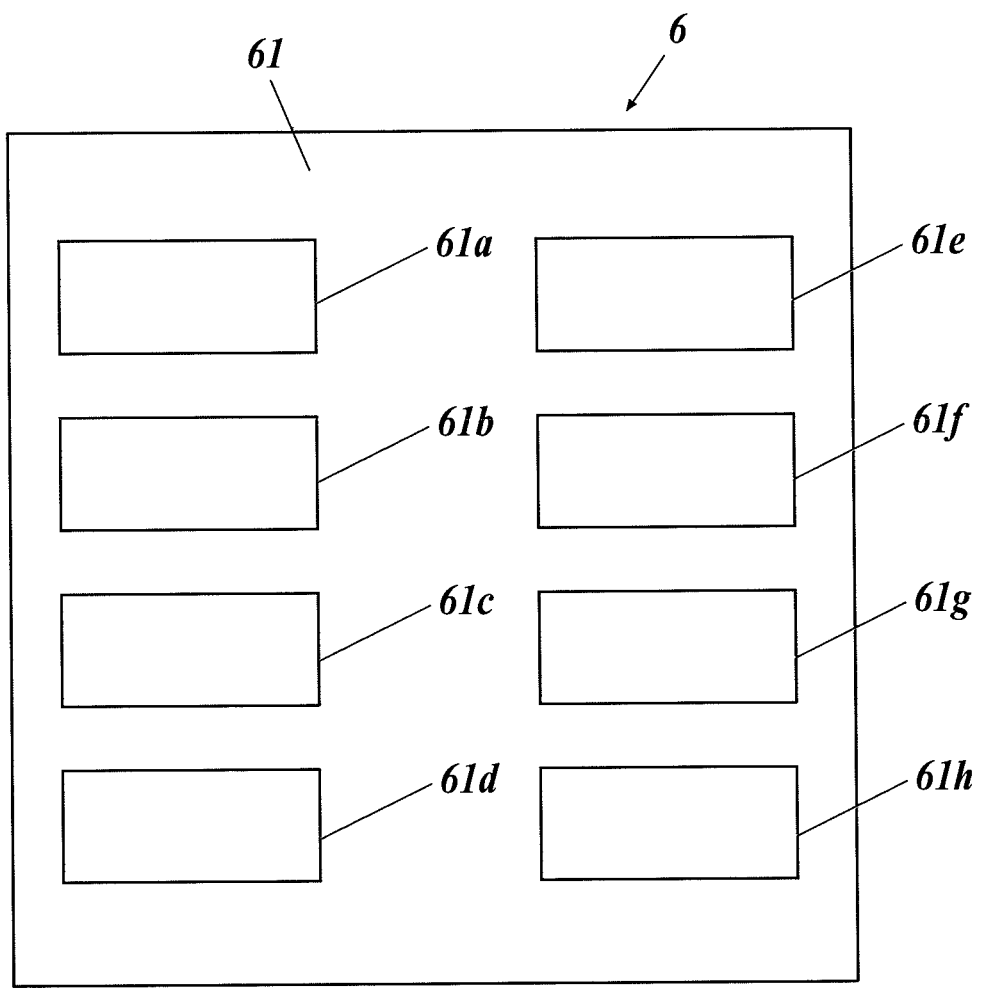
FIG. 4B is a schematic view of the back face of the TMR array module in accordance with the embodiment of the present invention.

As shown in FIG. 4, a TMR array module 6 includes a wiring substrate 61 having connector terminals 61a to 61h on the back face of the wiring substrate 61, and a TMR array module unit 62 configured on the front face of the wiring substrate 61. As shown in FIG. 3B, the TMR array module 6 is installed in such a way that the back face of the wiring substrate 61 is on the sensor platform board 41. The TMR array modules 6 are arranged in a matrix on the sensor platform board 41.

As shown in FIG. 4A, the TMR array module 6 is equipped with TMR array chips 63X, 63Y and 63Z.

FIG. 4A shows a three dimensional X-Y-Z Cartesian coordinate system. The TMR array chip 63X is a sensor module which measures a magnetic force in a plane in an X-axis direction, the plane being parallel to the front face of the wiring substrate 61 of the TMR array module 6. The TMR array chip 63Y is a sensor module which measures a magnetic force in the plane in a Y-axis direction, which is perpendicular to the X-axis direction, the plane being parallel to the front face of the wiring substrate 61 of the TMR array module 6. The TMR array chip 63Z is a sensor module which measures a magnetic force in a Z-axis direction, which is perpendicular to the front face of the wiring substrate 61 of the TMR array module 6.

Figure 5:
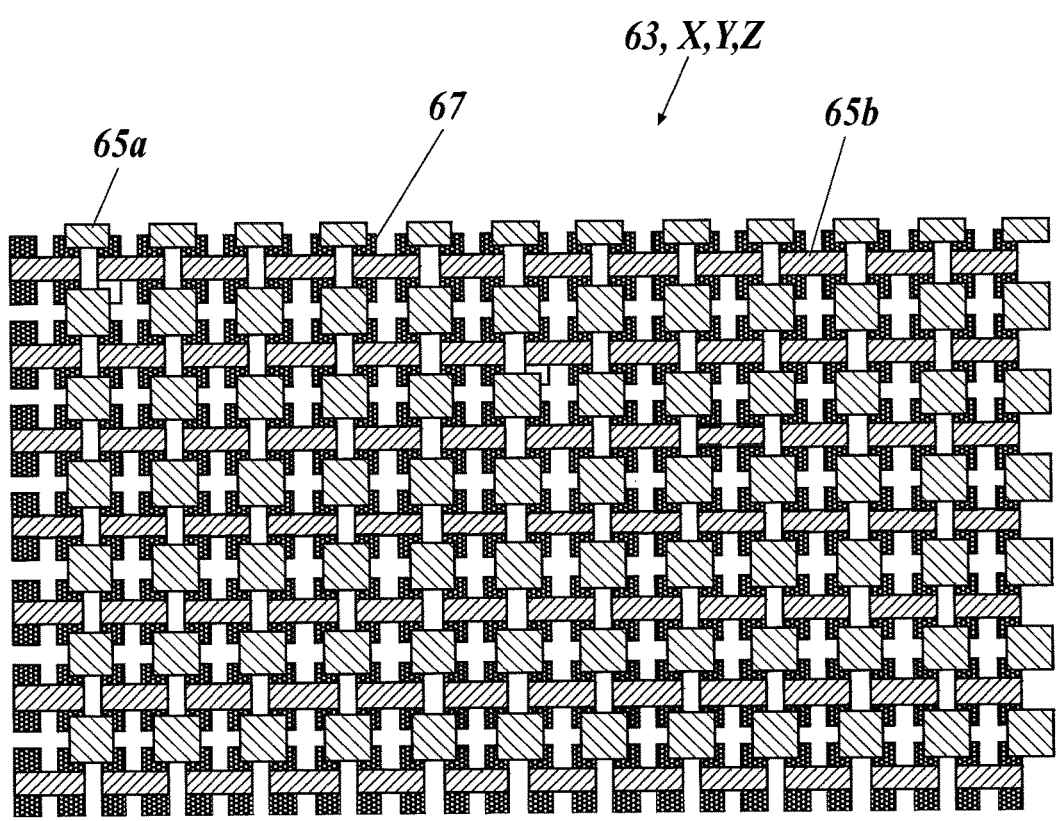
FIG. 5 is a layout chart showing a part of a TMR array in detail in accordance with the embodiment of the present invention.

As shown in FIG. 5, each of the TMR array chips 63X, 63Y and 63Z is configured in such a way that many basic configurations of upper electrodes 65a and lower electrodes 65b sandwiching TMR elements 67 are arranged in an array.

Figure 6:
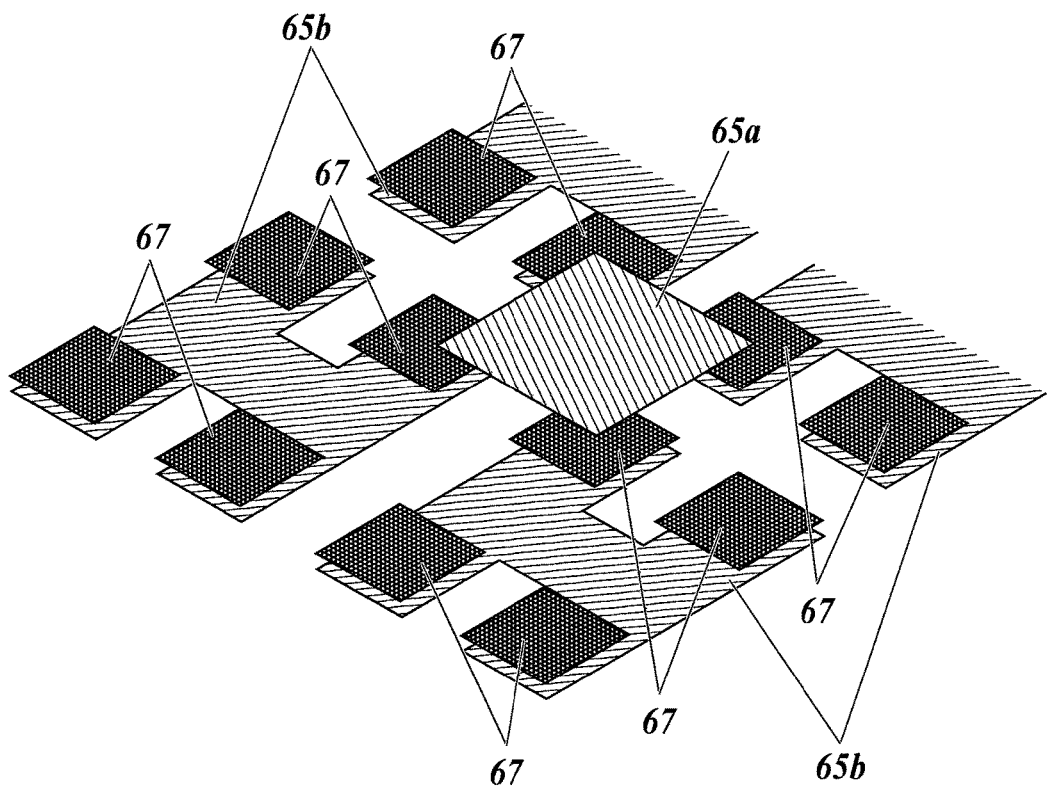
FIG. 6 is an illustration for explaining the layout of the TMR array in accordance with the embodiment of the present invention.
Figure 7:
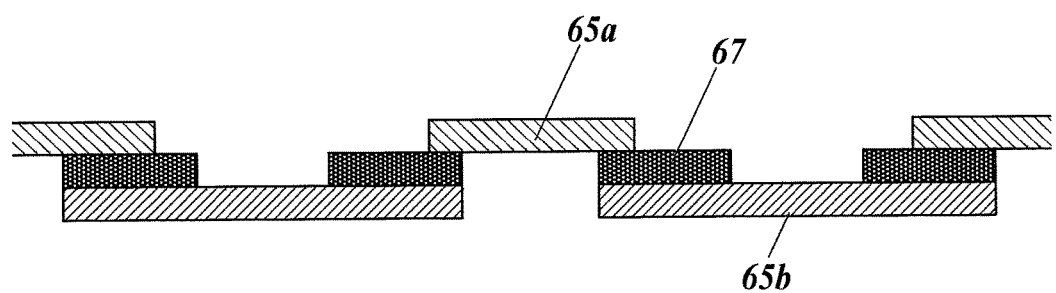
FIG. 7 is an illustration for explaining the layout of the TMR array in accordance with the embodiment of the present invention.

As schematically shown in FIG. 6, a shared upper electrode 65a is provided for four TMR elements 67. Each of the four TMR elements 67 makes a group with other three surrounding TMR elements 67, and a shared lower electrode 65b is provided for these four TMR elements 67 of the group. As shown in FIG. 7, in a cross sectional direction of the elements, the lower electrode 65b faces one face of a pair of a TMR element 67 and an adjacent TMR element 67, and the upper electrode 65a faces the other face of one TMR element 67 of the pair and another adjacent TMR element 67. By repeating such a configuration, many TMR elements 67 are electrically connected to each other by the upper electrodes 65a and the lower electrodes 65b. In FIG. 6, to be easily understood, only one upper electrode 65a is shown, and the other upper electrodes 65a are omitted.

Figure 8A:
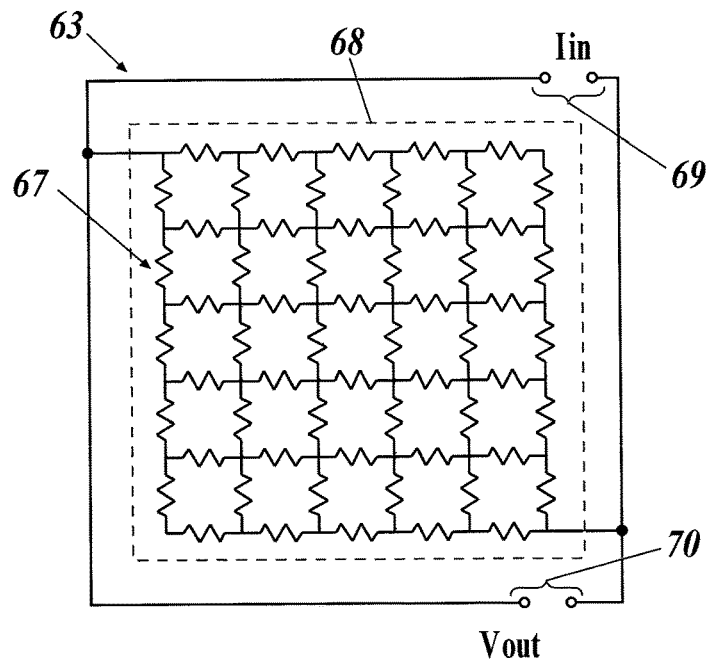
FIG. 8A is an electrical diagram of the TMR array in accordance with the embodiment of the present invention.

If an equivalent circuit of a TMR array chip 63 is shown with TMR elements 67 as resistors, its circuit diagram is as shown in FIG. 8A. This circuit constitutes a magnetic sensor which outputs a single output signal. As shown in FIGS. 5 and 8, the TMR elements 67 are arranged in a lattice so as to constitute a TMR array 68. As shown in FIG. 8, the TMR elements 67 are arranged in a lattice between current input terminals 69, which make a pair, and between voltage detection terminals 70, which make a pair. Portions to take out the terminals can be configured by an equivalent circuit of a TMR array chip 63B having individual connecting points for the terminals to the array as shown in FIG. 8B, and hence not limited to the form having shared connecting points for the terminals to the TMR array as shown in FIG. 8A.

Figure 8B:
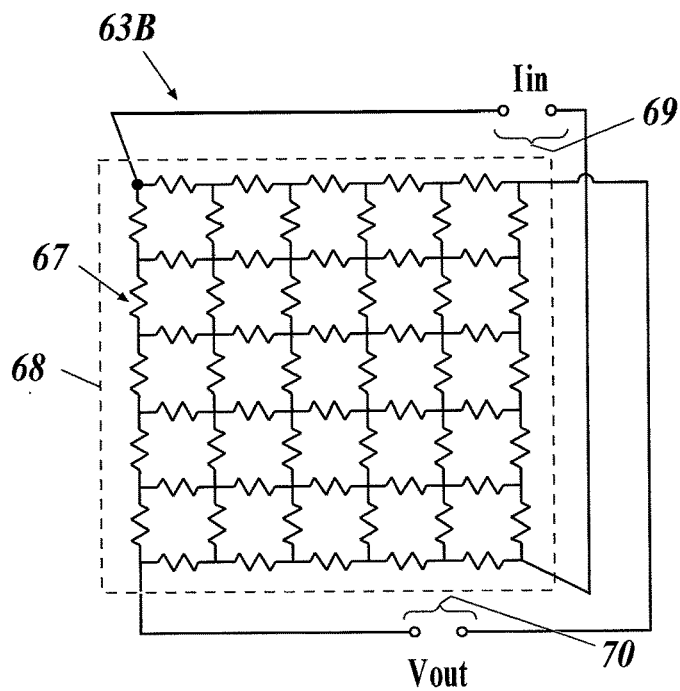
FIG. 8B is an electrical diagram of a TMR array in accordance with another embodiment of the present invention.

In FIGS. 8A and 8B, for making it simple, the array of 6×6 elements is shown. However, it has been found that if there are around 50×50 elements in practice, a noise level is reduced to 1/50 as compared with a noise level of one element. In the measurement of a brain's magnetic field, it is preferable that the number of elements of an array be 50×50 or more to reduce the noise level at least to 1/50 or lower, and more preferable that the number thereof be 100×100 or more to reduce the noise level to 1/100 or lower.

The pair of current input terminals 69 of each of the TMR array chips 63X, 63Y and 63Z is led to the connector terminals 61a and 61e. The pair of voltage detection terminals 70 of the TMR array chip 63X for the X axis is led to the connector terminals 61b and 61f. The pair of voltage detection terminals 70 of the TMR array chip 63Y for the Y axis is led to the connector terminals 61c and 61g. The pair of voltage detection terminals 70 of the TMR array chip 63Z for the Z axis is led to the connector terminals 61d and 61h. Wiring of the led lines of the terminals depends on wiring patterns in a not-shown bonding wire and the wiring substrate 61.

Thus, each of the TMR array chips 63X, 63Y and 63Z constitutes one magnetic sensor. In the embodiment, the TMR array module has three magnetic sensors so as to constitute magnetic sensors which can perform the measurement in three axes.

Figure 9:
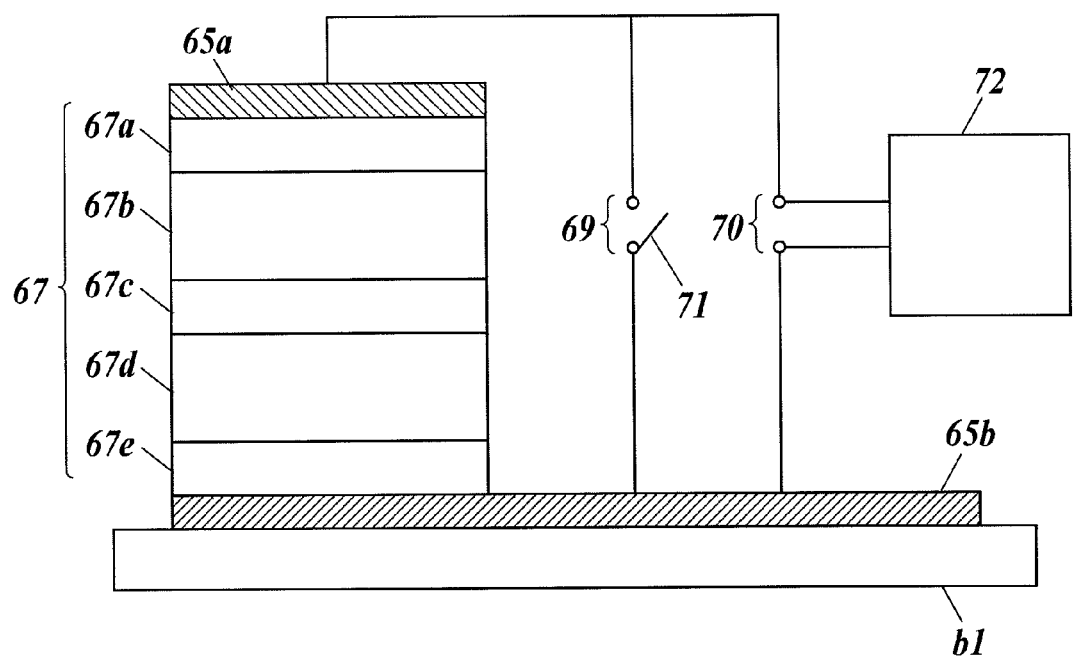
FIG. 9 is a schematic view showing a basic configuration of a TMR element (tunnel magneto-resistive element) in accordance with the embodiment of the present invention.

Each TMR element 67 has a basic configuration shown in FIG. 9. As shown in FIG. 9, the TMR element 67 has a configuration in which a lower electrode 65b, an antioxidation layer 67e, a free magnetic layer 67d, an insulating layer 67c, a fixed magnetic layer 67b, an antioxidation layer 67a and an upper electrode 65a are stacked on a substrate b1 in the order named. Between the upper electrode 65a and the lower electrode 65b, the current input terminals 69 connected to a current source 71 to input a current, and the voltage detection terminals 70 connected to a voltmeter 72 to detect a change of a resistance value of the insulating layer as a change of a voltage value are disposed. The change of a resistance value of the insulating layer may be detected by applying a voltage to the TMR element, and detecting a current flowing in the insulating layer of the TMR element.

Figure 10:
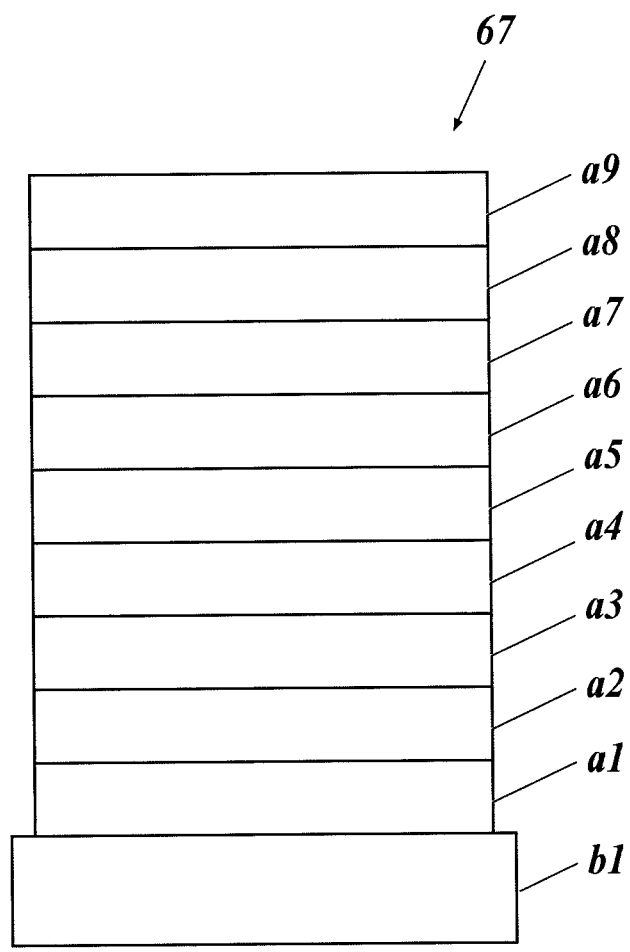
FIG. 10 is a cross-sectional view showing layers of the TMR element in accordance with the embodiment of the present invention.

A more specific configuration of each TMR element 67 is shown in FIG. 10 as an example. As shown in FIG. 10, each TMR element 67 has a configuration in which an undercoating layer a1, an auxiliary fixation layer a2, a fixation facilitation layer a3, fixed magnetic layers a4 to a6, an insulating layer a7, a free magnetic layer a8 and an antioxidation layer a9 are stacked on a substrate b1. Of the fixed magnetic layer, the layer a4 is a fixation layer, the layer a5 is a magnetic coupling facilitation layer, and the layer a6 is a ferromagnetic layer. The free magnetic layer includes the ferromagnetic layer a8. The fixed magnetic layer contacts the upper face of the insulating layer, and a direction of magnetization of the fixed magnetic layer is fixed. The free magnetic layer contacts the lower face of the insulating layer, and a direction of magnetization of the free magnetic layer is changed by being influenced by a magnetic flux from outside.

Although a material of the substrate b1 is not particularly limited as long as being able to withstand formation of the layers, it is preferable that the material thereof have a heat-resisting property and an insulating property so that the substrate b1 can withstand deposition of the layers, heat treatments and the like. Further, it is preferable that the material thereof be nonmagnetic in order to prevent the substrate b1 from absorbing the magnetic flux, and can make the surface of the substrate b1 relatively smooth. From these perspectives, for example, Si, SiO2 or the like can be used.

The undercoating layer a1 is to correct roughness of the substrate, and, for example, Ta can be used. It is preferable that the thickness of the undercoating layer a1 be about 2 nm to 10 nm.

The auxiliary fixation layer a2 is to assist orientation of the fixation facilitation layer a3, and Ru or permalloy can be used. In terms of further fixing the fixed magnetic layer, Ru is preferred. The crystal structure of the auxiliary fixation layer a2 is, for example, a hexagonal close-packed structure. It is preferable that the thickness of the auxiliary fixation layer a2 be about 5 nm to 20 nm.

The fixation facilitation layer a3 is to facilitate fixation of the fixation layer a4, and an antiferromagnetic film of IrMn, platinum manganese or the like is suitably used. The crystal structure of the fixation facilitation layer a3 is, for example, a face-centered cubic. It is preferable that the thickness of the fixation facilitation layer a3 be about 5 nm to 20 nm.

As the fixation layer a4, which constitutes the fixed magnetic layer, for example, CoFe can be used. The composition ratio of Co to Fe can be appropriately set. However, typically, it can be Co:Fe=75:25 or Co:Fe=50:50. The crystal structure of the fixation layer a4 is, for example, a face-centered cubic. It is preferable that the thickness of the fixation layer a4 be about 0.5 nm to 5 nm.

The magnetic coupling facilitation layer a5 is to magnetically couple the fixation layer a4 with the ferromagnetic layer a6, and also to separate the latter from the crystal structure of the former, and it is preferable to use a thin film layer not having a crystal structure. As an example of a specific material, Ru can be given. It is preferable that the thickness of the magnetic coupling facilitation layer a5 be about 0.5 nm to 1 nm.

As the ferromagnetic layer a6, various substances can be used. As a representative thereof, a substance obtained by performing a heat treatment on $Co_{40}Fe_{40}B_{20}$ from the amorphous structure so as to express ferromagnetism can be used. The crystal structure of the layer is, for example, a body-centered cubic. A material rich in Fe, such as $Co_{16}Fe_{64}B_{20}$, also can be used. It is preferable that the thickness of the ferromagnetic layer a6 be about 1 nm to 10 nm.

As the insulating layer a7, various insulating materials can be used. For example, MgO, AlOx or the like can be used. In terms of improving sensitivity of the element, MgO is preferred. It is preferable that the thickness of the insulating layer a7 be about 1 nm to 10 nm.

As the free magnetic layer a8, as is the case with the ferromagnetic layer a6, for example, $Co_{40}Fe_{40}B_{20}$ can be used. It is preferable that the thickness of the free magnetic layer a8 be about 1 nm to 10 nm. The free magnetic layer a8 may be multi-layered.

Each layer can be formed, for example, by a magnetron sputtering method. A heat treatment, such as annealing, may be performed as needed in order to obtain a desired crystal structure or the like.

Positions of the fixed magnetic layer and the free magnetic layer may be reversed from the positions thereof shown in the drawings. Further, the element may have a double junction configuration in which a free magnetic layer is sandwiched between two fixed magnetic layers through their respective insulating layers.

In the embodiment, the TMR element is produced by stacking 5 nm Ta as the layer a1, 10 nm Ru as the layer a2, 10 nm IrMn as the layer a3, 2 nm CoFe as the layer a4, 0.85 nm Ru as the layer a5, 3 nm $Co_{40}Fe_{40}B_{20}$ as the layer a6, 2 nm MgO as the layer a7, 3 nm $Co_{40}Fe_{40}B_{20}$ as the layer a8 and 5 nm Ta as the layer a9 on an $SiO_2$ substrate in the order named by using a magnetron sputtering device. The thickness of each layer is calculated from a deposition speed and a deposition time.

Such a TMR element can be suitably used for highly sensitive biomagnetism measurement near a zero magnetic field, and can accurately measure the magnetism emitted from a living body. Further, the TMR element is a magnetic sensor which can be used at a normal temperature, and neither a refrigerant for cooling nor a heat insulator for preventing heat from entering from outside is needed, so that the sensor unit can be configured lighter and thinner. Because the sensor unit can be configured lighter and thinner, the sensor unit can be configured in a simple and flexible form so as to be able to be handled by hand, and be placed on and cover a measurement target part of a subject, or be worn by a subject. Accordingly, regardless of the body size or the body shape of a subject, the TMR elements can be disposed so as to keep a certain distance to the target part, and the measurement can be performed accurately. Further, as compared with the SQUID sensors, the TMR elements can be configured at lower costs, and have lower power consumption.

In each of the TMR array chips 63X, 63Y and 63Z, bonding faces of the TMR elements 67 face in the same direction. Further, in each of the TMR array chips 63X, 63Y and 63Z, the directions of magnetization of the fixed magnetic layers are the same direction.

The directions of magnetization of the fixed magnetic layers of the TMR elements 67 of the TMR array chip 63X for the X axis, the directions of magnetization of the fixed magnetic layers of the TMR elements 67 of the TMR array chip 63Y for the Y axis and the directions of magnetization of the fixed magnetic layers of the TMR elements 67 of the TMR array chip 63Z for the Z axis are at right angles to each other.

The bonding faces of the TMR elements 67 of the TMR array chip 63X for the X axis and the bonding faces of the TMR elements 67 of the TMR array chip 63Y for the Y axis are disposed parallel to the wiring substrate 61. The bonding faces of the TMR elements 67 of the TMR array chip 63Z for the Z axis are disposed perpendicular to the wiring substrate 61.

In FIG. 4A, the TMR array chip 63Z for the Z axis is divided into two chips, but these chips may be configured as one chip.

Thus, because the TMR elements do not need cooling mechanisms, and can make distances between the magnetic sensors shorter, the degree of freedom in disposition thereof is high, and the measurement in the directions of three axes can be performed by disposing the magnetic sensors in such a way as to measure the magnetic fields in different directions. Accordingly, not only in a direction of one axis, such as a direction perpendicular to the surface of a living body, the direction in which the magnetism emitted from the living body is measured by the conventional SQUID sensors, but in directions of three axes, which are, for example, the direction of one axis perpendicular to the surface of a living body and directions of two axes at right angles to each other being in-plane directions of the surface of the living body, the magnetic forces of the magnetism can be measured. Hence, it becomes possible to obtain more magnetism information, and use the magnetism information for diagnosis. It is known that the magnetic fluxes emitted from a human body are various in directions. Information on the magnetic fluxes in various directions, which cannot be measured by the SQUID sensors, can be obtained.

Figure 11:
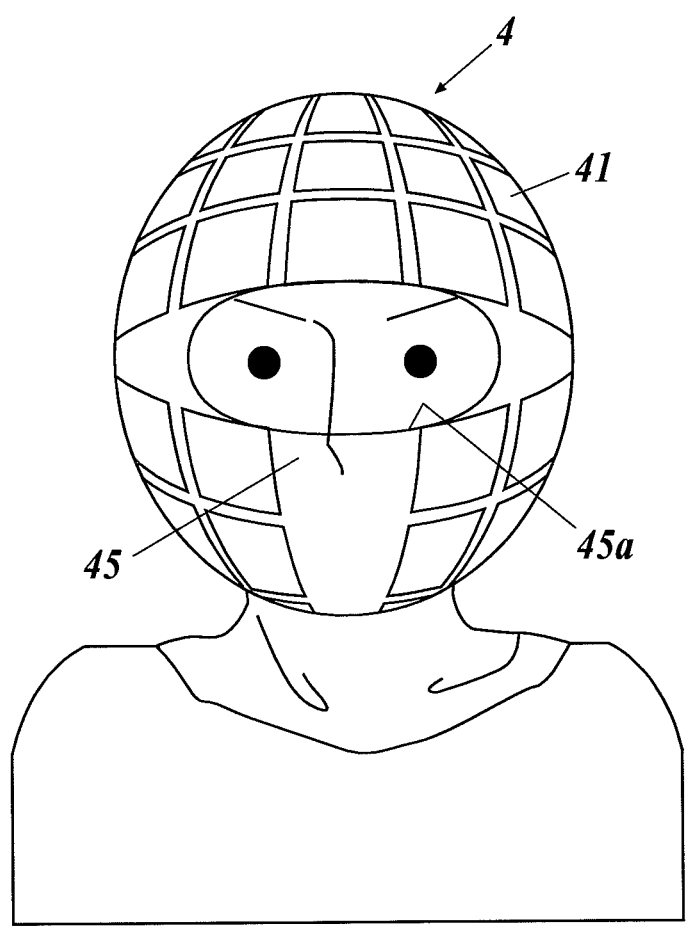
FIG. 11 is an illustration showing a state in which a sensor unit in accordance with the embodiment of the present invention is worn.

As shown in FIG. 11, the sensor unit 4 can be placed on and removed from a head part of a person, and is configured as one unit by a wearing support 45, which supports the sensor platform boards 41. As the wearing support 45, a wearing support which is made of an elastic material, such as fibers or resin, and, as shown in FIG. 11, is a ski mask type provided with holes 45a for eyes, and covering a head part and a face part can be used, for example. In this case, the brain's magnetism emitted not only from the head part but also from the face part can be measured. A wearing support 45 which covers a head part and a face part including eyes without providing the holes 45a may be configured.

A large number of sensor platform boards 41 are disposed along the wearing support 45. Consequently, many magnetic sensors are distributed on a shared face (the inner face of the wearing support 45 in FIG. 11), which is a face of the sensor unit 4, the face covering a head part of a person.

As shown in FIG. 11, the sensor unit 4 is placed on a head part of a person so as to be worn in such a way that the inner face of the wearing support 45 touches and is along the surface of the head part, so that the shared face is along the surface of the head part, many TMR elements 67 are disposed close to the surface of the head part, and many magnetic sensors are distributed on the surface of the head part.

In the embodiment, as the wearing support, the wearing support which supports a plurality of sensor platform boards, and which is placed on a head part of a person to be worn in such a way that the sensor platform boards are disposed along the surface of the head part is used. However, this is not a limitation. Each sensor platform board may be provided with a support member, such as a sucker or an adhesive layer, and attached to a head part of a living body.

In a state in which the sensor unit 4 is placed on a head part of a living body as described above, the following measurement is performed.

First, power is inputted into the whole system 100 constituted of the biomagnetism measuring device 1 and the arithmetic device 2, so that a current is inputted into each TMR array 68 from the current input terminals 69. In each TMR element 67 of the TMR array 68, the direction of magnetization of the free magnetic layer is changed by being influenced by a magnetic flux emitted from a head part of a person. Consequently, resistance of the insulating layer is changed by a tunnel effect depending on an angle difference between the direction of magnetization of the fixed magnetic layer and the direction of magnetization of the free magnetic layer. Hence, a voltage between the voltage detection terminals 70 of the TMR array 68 is changed, and this is the output signal in accordance with the change of the resistance of the TMR array 68. The factors which cause the change of the resistance of a single TMR element 67 are not only the magnetic flux but many others, and appear as noises, such as a heat noise and a shot noise.

However, the change of the resistance of the TMR array 68 is a value obtained by reducing these noises, and hence the output signal of the TMR array 68 is a highly dependable value in accordance with the change of the magnetic flux. Its theoretical proof is described in the non-patent documents 1 and 2.

Next, an operator inputs a measurement execution command into the arithmetic device 2.

The arithmetic device 2 sends out the measurement execution command to n sensor platform boards 41. Each sensor platform board 41 receives the measurement execution command with the controller 42.

The controller 42 receives the output signal of each TMR array 68, the output signal being digitalized via the amplifier & converter circuit 44, and sends out, as biomagnetism measurement information, the output signal in a predetermined format in which the output signal is linked with address information on the TMR array 68 and information identifying the X, Y or Z direction of the TMR array 68 to the arithmetic device 2.

The arithmetic device 2 analyzes the biomagnetism measurement information sent from each controller 42, calculates a magnetoencephalogram constituted of a position on a head part of a subject, strength of magnetism thereon and a direction of the magnetism, which are combined, makes the biomagnetism measurement information image information, and displays and outputs the image information on the display device 21.

The arithmetic device 2 generates a composite image in which the image of the biomagnetism measurement information, an MRI image of the head part of the subject, a three-dimensional scan image and the like are superimposed on top of each other with their positions aligned, and displays and outputs the composite image on the display device 21.

The measurement execution command may be one measurement execution command, or may be a measurement starting command and a measurement ending command. What is effective is that the measurement is performed at a predetermined time rate during a period of time from the measurement starting command to the measurement ending command, and a magnetoencephalogram, which changes in real time, is displayed on the display device 21.

The biomagnetism measurement information, the magnetoencephalogram information and the image information generated for display are recorded in such a way as to be readable by the arithmetic device 2, so as to be displayed or replayed on the display device 21.

In the embodiment described above, a head part of a person is a measurement target. However, this is not a limitation, and hence another part of a living body may be a measurement target. For example, a chest part of a person may be a measurement target so that a magnetic image of the chest part is obtained.

In the embodiment described above, the biomagnetism is detected in directions of three axes. Accordingly, as compared with the SQUID sensors, which can measure the magnetism emitted in a direction perpendicular to the surface of a living body only, it becomes possible to obtain more magnetism information, and use the magnetism information for diagnosis. However, this is not a limitation, and the magnetism may be detected in a direction of one axis or directions of two axes. In the case of the direction of one axis only, it is preferable that the direction be a direction perpendicular to the surface of a living body (the X-axis direction). In the case of the directions of two axes, it is preferable that the directions be the direction perpendicular to the surface of a living body (the X-axis direction) and a direction parallel to the surface of the living body (the X-axis direction or the Y-axis direction). In the case of the directions of two axes, a magnetic sensor may include a first tunnel magneto-resistive element array in which the direction of magnetization of the fixed magnetic layer is fixed in a first direction, and a second tunnel magneto-resistive element array in which the direction of magnetization of the fixed magnetic layer is fixed in a second direction which intersects with the first direction.

INDUSTRIAL APPLICABILITY

The present invention can be used for obtaining the magnetism information, such as magnetoencephalograms and magnetocardiograms, by measuring the magnetism emitted from a living body.

EXPLANATION OF REFERENCES

1 biomagnetism measuring device
2 arithmetic device
3 interface
4 sensor unit
5 cable
6 TMR array module (magnetic sensor)
21 display device
41 sensor platform board (sensor assembly)
42 controller
44 amplifier & converter circuit
45 wearing support
51 power line
52 signal line
61 wiring substrate
61*a* connector terminal
61*b* connector terminal
62 TMR array module unit
63 TMR array chip (magnetic sensor)
64 adhesive layer
65*a* upper electrode
65*b* lower electrode
66 bonding wire
67 TMR element
68 TMR array
69 current input terminal
70 voltage detection terminal
100 biomagnetism measuring system

The invention claimed is:

1. A biomagnetism measuring device comprising:
a magnetic sensor including:
a plurality of tunnel magneto-resistive elements, each of said plurality of tunnel magneto-resistive elements including:
a fixed magnetic layer in which a direction of magnetization is fixed;
a free magnetic layer in which a direction of magnetization is changed by being influenced by a magnetic flux from outside; and
an insulating layer disposed between the fixed magnetic layer and the free magnetic layer, and having resistance being changed by a tunnel effect depending on an angle difference between the direction of the magnetization of the fixed magnetic layer and the direction of the magnetization of the free magnetic layer; and
a support unit made of an elastic material which supports the magnetic sensor such that the plurality of tunnel magneto-resistive elements are adapted to face a living body
wherein the plurality of tunnel magneto-resistive elements are arranged as:
a first tunnel magneto-resistive element array in which the direction of the magnetization of the respective fixed magnetic layers are fixed in a first direction,
a second tunnel magneto-resistive element array in which the direction of the magnetization of the respective fixed magnetic layers are fixed in a second direction which intersects with the first direction, and
a third tunnel magneto-resistive element array in which the direction of the magnetization of the respective fixed magnetic layers are fixed in a third direction which is at right angles to the first direction and the second direction, the first, second and third tunnel magneto-resistive element arrays being configured in individual chips, and each of said individual chips being mounted on the same wiring substrate,
wherein each tunnel magneto-resistive array outputs an output signal in accordance with a resistance value of the insulating layer of each of the plurality of tunnel magneto-resistive elements in the respective tunnel-magneto-resistive array, the resistance value being configured to be changed by magnetism emitted from the living body,
wherein the support unit has a shape configured to surround a measurement target part of the living body and is adapted to cover the measurement target part and a vicinity of the measurement target part, and is further adapted to partially or entirely touch a surface of the living body at the measurement target part and/or the vicinity of the measurement target part so that the biomagnetism measuring device can be worn by the living body,
wherein the plurality of tunnel magneto-resistive elements are connected in a lattice in the first, second and third tunnel magneto-resistive element arrays, and the output signal from each tunnel magneto-resistive array is output from a shared output terminal provided for the plurality of tunnel magneto-resistive elements in each tunnel magneto-resistive array,
wherein bonding faces of fixed magnetic layers and insulating layers and/or bonding faces of free magnetic layers and insulating layers of the plurality of tunnel magnetoresistive elements of the respective tunnel magneto-resistive element array are disposed on a shared plane,
wherein the shared plane of the first tunnel magneto-resistive element array is adapted along a direction perpendicular to a measurement target part of the living body,
wherein the plurality of tunnel magneto-resistive elements are connected in the lattice between two shared output terminals provided for the respective tunnel magneto-resistive element array to output the output signal; and
wherein, on a substrate in a chip in which the tunnel magneto-resistive element arrays are configured, groups of tunnel magneto-resistive elements are formed in two rows of two tunnel magneto-resistive elements which share a shared lower electrode among the tunnel magneto-resistive elements of a respective group, the groups being repeatedly arranged lengthwise and breadthwise, wherein four tunnel magneto-resistive elements of four different groups that are not sharing a shared lower electrode share a shared upper electrode, such that the plurality of tunnel magneto-resistive elements are connected in the lattice between the two shared output terminals.

2. A biomagnetism measuring method comprising:
supporting a magnetic sensor with a support unit such that a plurality of tunnel magneto-resistive elements are adapted to face a living body, the magnetic sensor including the plurality of tunnel magneto-resistive elements, each element of the plurality of tunnel magneto-resistive elements including:
a fixed magnetic layer in which a direction of magnetization is fixed;
a free magnetic layer in which a direction of magnetization is changed by being influenced by a magnetic flux from outside; and
an insulating layer disposed between the fixed magnetic layer and the free magnetic layer, and having resistance being changed by a tunnel effect depending on an angle difference between the direction of the magnetization of the fixed magnetic layer and the direction of the magnetization of the free magnetic layer;
wherein the support unit has a shape configured to surround a measurement target part of the living body and is adapted to cover the measurement target part and a vicinity of the measurement target part, and is adapted to partially or entirely touch a surface of the living body at the measurement target part and/or the vicinity of the measurement target part so that the biomagnetism measuring device is configured to be worn by the living body,
wherein the magnetic sensor further includes the plurality of tunnel magneto-resistive elements arranged as a first tunnel magneto-resistive element array in which the direction of the magnetization of the respective fixed magnetic layers are fixed in a first direction, a second tunnel magneto-resistive element array in which the direction of the magnetization of the respective fixed magnetic layers are fixed in a second direction which intersects with the first direction, and a third tunnel magneto-resistive element array in which the direction of the magnetization of the respective fixed magnetic layers are fixed in a third direction which is at right angles to the first direction and the second direction, the first, second and third tunnel magneto-resistive element arrays being configured in individual chips, and each of said individual chips being mounted on the same wiring substrate, wherein the plurality of tunnel magneto-resistive elements are connected in a lattice in the first, second and third tunnel magneto-resistive element arrays, and each tunnel magneto-resistive array outputs an output signal from a shared output terminal provided for the plurality of tunnel magneto-resistive elements in each tunnel magneto-resistive array, wherein bonding faces of fixed magnetic layers and insulating layers and/or bonding faces of free magnetic layers and insulating layers of the plurality of tunnel magneto-resistive elements of the respective tunnel magneto-resistive element array are disposed on a shared plane, wherein the shared plane of the first tunnel magneto-resistive element array is adapted along a direction perpendicular to a measurement target part of the living body, and measuring magnetism of the living body based on the output signals, wherein each output signal is in accordance with a resistance value of the insulating layer of each of the plurality of tunnel magneto-resistive elements in the respective tunnel magneto-resistive array, the resistance value being configured to be changed by the magnetism emitted from the living body;

wherein the plurality of tunnel magneto-resistive elements are connected in the lattice between two shared output terminals provided for the respective tunnel magneto-resistive element array to output the output signal; and wherein, on a substrate in a chip in which the tunnel magneto-resistive element arrays are configured, groups of tunnel magneto-resistive elements are formed in two rows of two tunnel magneto-resistive elements which share a shared lower electrode among the tunnel magneto-resistive elements of a respective group, the groups being repeatedly arranged lengthwise and breadthwise, wherein four tunnel magneto-resistive elements of four different groups that are not sharing a shared lower electrode share a shared upper electrode, such that the plurality of tunnel magneto-resistive elements are connected in the lattice between the two shared output terminals.

* * * * *